(12) United States Patent
Williams et al.

(10) Patent No.: US 8,372,325 B2
(45) Date of Patent: Feb. 12, 2013

(54) HIGHLY CONVERTIBLE ENDOLUMENAL PROSTHESES AND METHODS OF MANUFACTURE

(75) Inventors: Michael S. Williams, Santa Rosa, CA (US); Robert S. Langer, Newton, MA (US); Yadong Wang, Mableton, GA (US)

(73) Assignee: SyneCor LLC, Chapel Hill, NC (US)

( * ) Notice: Subject to any disclaimer, the term of this patent is extended or adjusted under 35 U.S.C. 154(b) by 649 days.

(21) Appl. No.: 12/148,895

(22) Filed: Apr. 22, 2008

(65) Prior Publication Data

US 2008/0281405 A1 Nov. 13, 2008

Related U.S. Application Data

(62) Division of application No. 10/988,814, filed on Nov. 15, 2004, now Pat. No. 7,377,939.

(60) Provisional application No. 60/523,578, filed on Nov. 19, 2003.

(51) Int. Cl.
*B29C 41/02* (2006.01)
*C08G 63/16* (2006.01)

(52) U.S. Cl. .................. 264/230; 264/331.18; 528/302

(58) Field of Classification Search .................. 264/230, 264/331.18
See application file for complete search history.

(56) References Cited

U.S. PATENT DOCUMENTS

| | | | | |
|---|---|---|---|---|
| 4,298,724 A * | 11/1981 | Sommerfeld et al. | ........ | 528/302 |
| 5,919,225 A | 7/1999 | Lau et al. | | |
| 5,964,744 A * | 10/1999 | Balbierz et al. | ................ | 604/530 |
| 6,152,141 A * | 11/2000 | Stevens et al. | ................ | 128/898 |
| 6,240,978 B1 | 6/2001 | Gianotti | | |
| 6,299,636 B1 | 10/2001 | Schmitt et al. | | |
| 6,388,043 B1 * | 5/2002 | Langer et al. | ................... | 528/80 |
| 6,444,782 B1 * | 9/2002 | Hamlin | ......................... | 528/300 |
| 7,316,710 B1 * | 1/2008 | Cheng et al. | ................. | 623/1.15 |
| 7,335,187 B2 * | 2/2008 | Altman | .................... | 604/164.08 |
| 7,794,645 B2 * | 9/2010 | Leonard et al. | .......... | 264/331.18 |

(Continued)

FOREIGN PATENT DOCUMENTS

| | | |
|---|---|---|
| JP | 03-118078 | 5/1991 |
| JP | 07-100156 A | 4/1995 |

(Continued)

OTHER PUBLICATIONS

Wang, Yadong, et al., In vivo degradation characteristics of poly(glycerol sebacate), J Biomed Mater Res 66A: 192-197, 2003, Wiley Periodicals Inc., U.S.A.

(Continued)

*Primary Examiner* — Joseph Del Sole
*Assistant Examiner* — Ryan Ochyliski
(74) *Attorney, Agent, or Firm* — Deanna Shirley Williams

(57) ABSTRACT

Endolumenal prostheses that readily and extensively convert from a delivery configuration to a deployed configuration are disclosed. Endolumenal prostheses may be fabricated from one or more shape memory polymers, a high modulus elastomer, a polymer that is both elastomeric and exhibits shape memory behavior, a hydrogel, or some combination thereof. Polymers used to fabricate the prostheses are selectively synthesized to exhibit desired characteristics such as crystallinity, strain fixity rate, strain recovery rate, elasticity, tensile strength, mechanical strength, cross-linking density, extent physical cross-linking, extent of covalent cross-linking, extent of interpenetrating networks, rate of erosion, heat of fusion, crystallization temperature, and acidity during erosion. The endolumenal prostheses convert to the deployed configuration following delivery to a treatment site, upon exposure to an initiator either present within the body naturally or introduced into the body.

7 Claims, 2 Drawing Sheets

U.S. PATENT DOCUMENTS

| | | | |
|---|---|---|---|
| 2001/0031370 A1* | 10/2001 | Kundel | 428/515 |
| 2002/0183449 A1* | 12/2002 | Okuhira | 525/100 |
| 2003/0100830 A1* | 5/2003 | Zhong et al. | 600/431 |
| 2004/0093073 A1* | 5/2004 | Lowe et al. | 623/1.15 |
| 2004/0143209 A1* | 7/2004 | Liu et al. | 604/8 |
| 2006/0147492 A1* | 7/2006 | Hunter et al. | 424/426 |

FOREIGN PATENT DOCUMENTS

| | | |
|---|---|---|
| JP | 10-309313 A | 11/1998 |

OTHER PUBLICATIONS

Lendlein, A. et al., Biodegradable, Elastic Shape Memory Polymers for Potential Biomedical Applications, Sciencexpress, www.sciencexpress.org/25 April 2002/Page 1/10.1126, USA.

Wang, Y., et al., A tough biodegradable elastomer, nature biotechnology, vol. 20, Jun. 2002, http://biotech.nature.com, U.S.A.

Landlein, A., et al., AB-polymer networks based on oligo(epsilon-caprolactone) segments showing shape-memory properties, PNAS, Jan. 30, 2001, vol. 98 No. 3, pp. 842-847, USA.

* cited by examiner

HIGHLY CONVERTIBLE ENDOLUMENAL PROSTHESES AND METHODS OF MANUFACTURE

RELATED APPLICATIONS

This application is a divisional of U.S. patent application Ser. No. 10/988,814, filed Nov. 15, 2004 now U.S. Pat. No. 7,377,939 by Williams et al., entitled "Highly Convertible Endolumenal Prostheses and Methods of Manufacture", which is related to and claims the benefit of the priority date of U.S. Provisional Patent Application Ser. No. 60/523,578 entitled "Highly Convertible Endolumenal Prostheses and Methods of Manufacture", filed Nov. 19, 2003. The above applications are commonly owned and hereby incorporated by reference, each in its entirety.

FIELD OF THE INVENTION

The invention herein relates generally to medical devices and the manufacture thereof, and to improved endolumenal prostheses for use in the treatment of strictures in lumens or ducts of the body. More particularly, the invention is directed to endolumenal prostheses comprising one or more polymers exhibiting one or more or a combination of shape memory, superelastic, or other properties, wherein such polymers are selectively isolated, produced, or synthesized to exhibit a range of desired mechanical and structural properties, such that the materials enter the body in a first configuration, and, upon exposure to body temperature or other environmental conditions, and/or additional external stimuli the materials convert readily into a second configuration to form the desired endolumenal prosthesis. The invention herein addresses the shortcomings of the prior art, especially, but not limited to, material limitations such as large delivery profile and insufficient conversion from a delivery configuration to a deployed configuration. In addition, the invention herein helps eliminate the need for manipulation of conditions required for deployment of prior art devices, enhancing facility of the device under the constraints of a clinical setting.

BACKGROUND OF THE INVENTION

Ischemic heart disease is the major cause of death in industrialized countries. Ischemic heart disease, which often results in myocardial infarction, is a consequence of coronary atherosclerosis. Atherosclerosis is a complex chronic inflammatory disease and involves focal accumulation of lipids and inflammatory cells, smooth muscle cell proliferation and migration, and the synthesis of extracellular matrix. *Nature* 1993; 362:801-809. These complex cellular processes result in the formation of atheromatous plaque, which consists of a lipid-rich core covered with a collagen-rich fibrous cap, varying widely in thickness. Further, plaque disruption is associated with varying degrees of internal hemorrhage and luminal thrombosis because the lipid core and exposed collagen are thrombogenic. *J Am Coll Cardiol.* 1994; 23:1562-1569 Acute coronary syndrome usually occurs as a consequence of such disruption or ulceration of a so called "vulnerable plaque". *Arterioscler Thromb Vasc Biol.* Volume 22, No. 6, June 2002, p. 1002.

In addition to coronary bypass surgery, a current treatment strategy to alleviate vascular occlusion includes percutaneous transluminal coronary angioplasty, expanding the internal lumen of the coronary artery with a balloon. Roughly 800,000 angioplasty procedures are performed in the U.S. each year (*Arteriosclerosis, Thrombosis, and Vascular Biology* Volume 22, No. 6, June 2002, p. 884). However, 30% to 50% of angioplasty patients soon develop significant restenosis, a narrowing of the artery through migration and growth of smooth muscle cells.

In response to the significant restenosis rate following angioplasty, percutaneously placed endolumenal prostheses have been extensively developed to support the vessel wall and to maintain fluid flow through a diseased coronary artery. Such endolumenal prostheses, or stents, which have been traditionally fabricated using metal alloys, include self-expanding or balloon-expanded devices that are "tracked" through the vasculature and deployed proximate one or more lesions. Stents considerably enhance the long-term benefits of angioplasty, but 10% to 50% of patients receiving stents still develop restenosis. *J Am Coll Cardiol.* 2002; 39:183-193. Consequently, a significant portion of the relevant patient population undergoes continued monitoring and, in many cases, additional treatment.

Continued improvements in stent technology aim at producing easily tracked, easily visualized and readily deployed stents, which exhibit the requisite radial strength without sacrificing both a small delivery profile and sufficient flexibility to traverse the diseased human vasculature and to permit sufficient non-injuring compliance with vessel walls. Further, predictable, easily controlled deployment diameter and non-injuring expansion of endoprostheses are needed.

In addition, numerous therapies directed to the cellular mechanisms of accumulation of inflammatory cells, smooth muscle cell proliferation and migration show tremendous promise for the successful long-term treatment of ischemic heart disease. Consequently, advances in coupling delivery of such therapies to the mechanical support of vascular endoprostheses, delivered proximate the site of disease, offer great hope to the numerous individuals suffering heart disease.

While advances in the understanding of ischemic heart disease as a complex chronic inflammatory process take place, traditional diagnostic techniques such as coronary angiography yield to next generation imaging modalities. In fact, coronary angiography may not be at all useful in identifying inflamed atherosclerotic plaques that are prone to producing clinical events. Imaging based upon temperature differences, for example, are undergoing examination for use in detecting coronary disease. Magnetic resonance imaging (MRI) is currently emerging as the state of the art diagnostic for arterial imaging, enhancing the detection, diagnosis and monitoring of the formation of vulnerable plaques. Transluminal intervention guided by MRI is expected to follow. However, metals produce distortion and artifacts in MR images, rendering use of the traditionally metallic stents in coronary, biliary, esophageal, ureteral, and other body lumens incompatible with the use of MRI.

Consequently, an emerging clinical need for interventional devices that are compatible with and complementary to new imaging modalities is evident. Further, devices that exhibit improved trackability to previously undetectable disease within remote regions of the body, especially the coronary vasculature are needed. And finally, devices that exhibit improved, continuous mechanical support and are readily compatible with adjunct therapies in order to lower or eliminate the incidence of restenosis are needed.

SUMMARY OF THE INVENTION

An endolumenal prosthesis is disclosed comprising one or more polymers, said endolumenal prosthesis comprising a delivery configuration and a deployed configuration, wherein said one or more polymers are synthesized to exhibit to a selected extent one or more properties selected from the group consisting of crystallinity, tensile strength, mechanical strength, modulus of elasticity, strain recovery rate, strain fixity rate, transition temperature, melting temperature, crystallization temperature, cross-linking density, extent of physical cross-linking, extent of covalent bond cross-linking, extent of formation of interpenetrating networks, rate of erosion, acidity during erosion, and heat of fusion. One or more of the polymers may comprise a shape memory polymer, one or more elastomer, or any combination thereof. An endolumenal prosthesis according to the invention may comprise one or more memory polymers synthesized from a first monomer and a second monomer, said first and second monomers selected to impart desired properties on said shape memory polymer. The first monomer may comprise a first molecular weight wherein said first molecular weight is a first parameter in determining said desired properties of said shape memory polymer.

One or more shape memory polymers used to fabricate an endolumenal prosthesis according to the invention may comprise one or more hard segments and one or more soft segments, said hard segments and soft segments formed from a first and second monomer and wherein said one or more hard segments comprises a first transition temperature, and said one or more soft segments comprises a second transition temperature.

An endolumenal prosthesis according to the invention may be fabricated from a polymer synthesized from oligo(ε-caprolactone) dimethacrylate and n-butyl acrylate, where said oligo(ε-caprolactone) dimethacrylate comprises a first molecular weight, and said first molecular weight comprises a first parameter for a desired property of said shape memory polymer. Oligo(ε-caprolactone) dimethacrylate may be combined with n-butyl acrylate in a ratio of between 30:70 and 80:20. Alternatively, the one or more shape memory polymers may be synthesized from oligo(ε-caprolactone) diol and oligo (p-dioxanone) diol, where oligo(ε-caprolactone) diol is a precursor for a switching segment and said oligo(p-caprolactone) diol is a precursor for a hard segment. The oligo(ε-caprolactone) diol may be coupled with said oligo(p-dioxanone) diol in a ratio of between 90:10 and 20:80.

Alternatively, the one or more polymers used to fabricate an endolumenal prosthesis according to the invention may be synthesized from one or more elastomeric blocks and one or more shape memory polymers. One or more polymers may be synthesized from poly(glycerol-sebacate) and one or more aromatic polymers, such as, for example, dimethyl terephthalate.

An endolumenal prosthesis according to the invention may be substantially erodible, may comprise a foreshortening ratio of less than 13%, and may comprise a surface area that is 18% of the total area of the exterior surface. The expansion ration may be between 20% and 400%, and the strain fixity rate and the strain recovery rate may be between 90% and 100%. The modulus of elasticity may be greater than 100.

One or more of the polymers used to fabricate a device according to the invention may be hydrophobic or hydrophilic, may be a hydrogel, or a thermoplastic elastomer, such as, for example, poly(glycerol terephthalate), or a thermoset.

An endolumenal prosthesis according to the invention may comprise a delivery configuration that is substantially non-tubular, and or substantially linear, and a deployed configuration that is generally tubular. It may convert from the delivery configuration to the deployed configuration upon exposure to one or more initiators, such as, for example, change in temperature, hydration, increased salinity, or radiation. It may produce stresses of between 0.10-10.0 MPa when converting from said delivery configuration to said deployed configuration, and radial strength equal to or greater than 300 mm Hg.

An endolumenal prosthesis according to the invention may comprise variable surface characteristics, such as, for example, means for engaging the interior or a body lumen, a roughened surface, or a first density and a second density, wherein said second density is greater than said first density.

A method of manufacturing a shape memory polymer endolumenal prosthesis according to the invention may comprise the steps of selecting a first monomer comprising a first set of characteristics that serves as a first parameter in determining the properties of a polymer; selecting a second monomer comprising a second set of characteristics that serves as a second parameter in determining the properties of a polymer, determining a desired ratio of said first monomer to said second monomer; synthesizing a polymer from said first and said second monomer, manufacturing a generally tubular endoprosthesis from said polymer; setting a permanent shape for said endoprosthesis; and setting a temporary shape for said endoprosthesis. The first and second sets of characteristics may comprise molecular weight, transition temperature, readiness to form physical crosslinks, readiness to form covalent bonds, and crystallinity. The properties of the polymer may comprise extent of physical crosslinks, extent of covalent bonds, extent of networking, tensile strength, transition temperature, melting temperature, strain recovery rate, strain fixity rate, modulus of elasticity, degree of crystallization, hydrophilicity and hydrophobicity. The first and second monomers may be selected from the group consisting of caprolactones, dioxanones, acrylates, linear aliphatic polyesters and ethers. The method may further comprise the step of laminating said endoprosthesis with a hydrogel after setting the temporary shape.

DETAILED DESCRIPTION OF THE INVENTION

Figure 1:
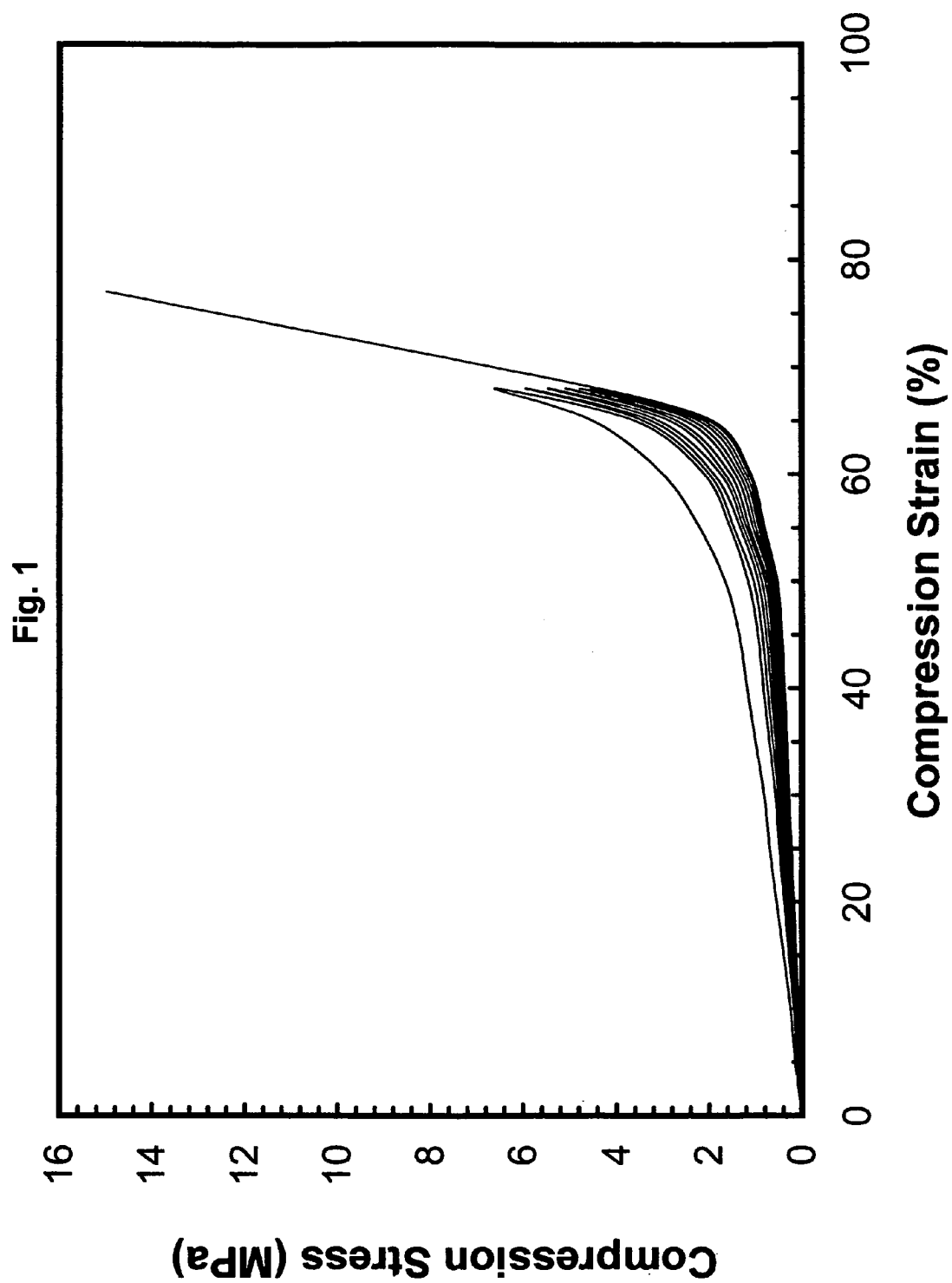
FIG. 1 is a graph illustrating the compressive stress-strain curve of a copolymer according to the invention.
Figure 2:
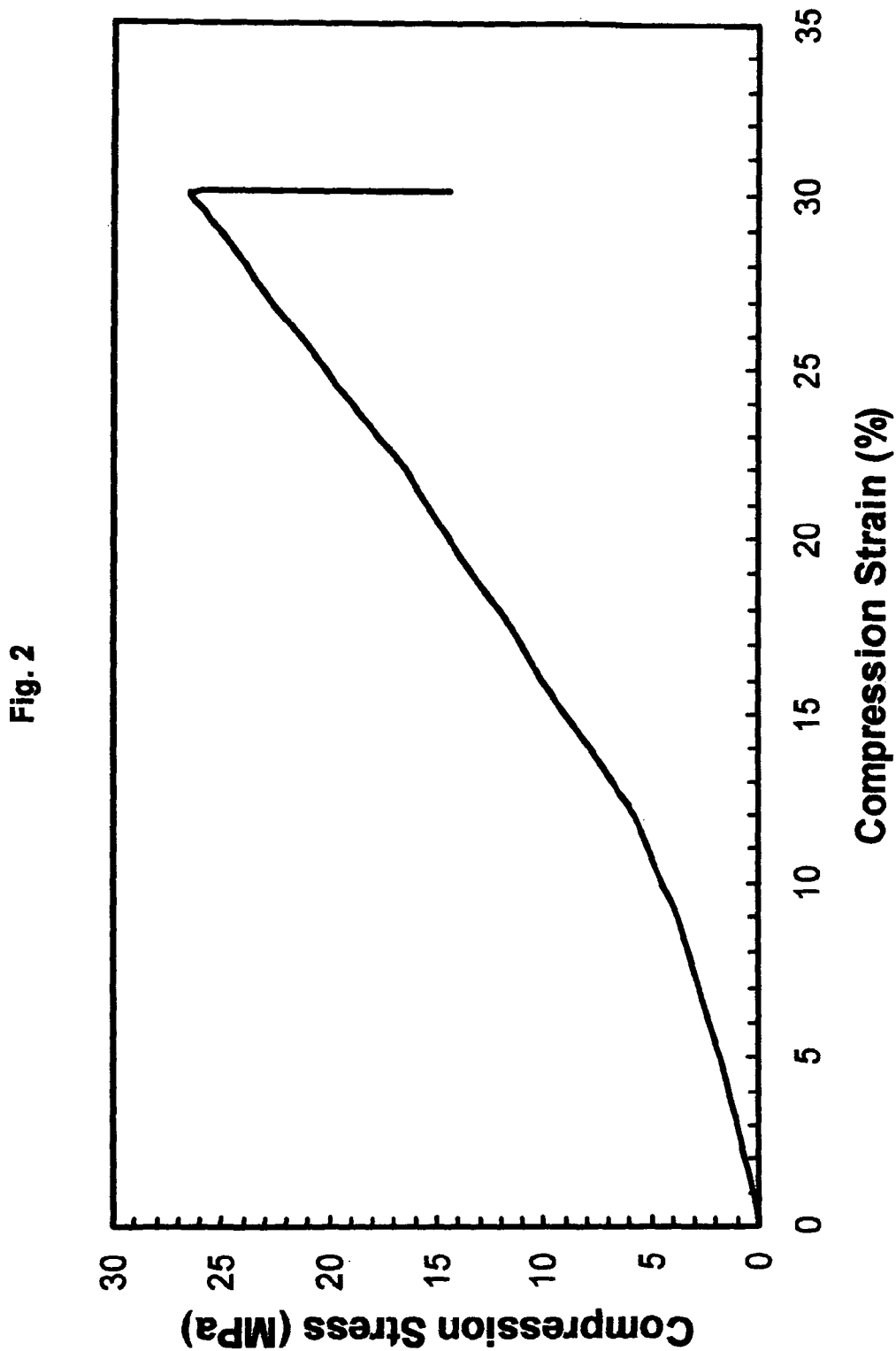
FIG. 2 is a graph illustrating the compressive stress-strain curve of an alternative copolymer according to the invention.

Although the invention herein is not limited as such, some embodiments of the invention comprise materials that are erodible. "Erodible" refers to the ability of a material to maintain its structural integrity for a desired period of time, and thereafter gradually undergo any of numerous processes whereby the material substantially loses tensile strength and mass. Examples of such processes comprise hydrolysis, enzymatic and non-enzymatic degradation, oxidation, enzymatically-assisted oxidation, and others, thus including bioresorption, dissolution, and mechanical degradation upon interaction with a physiological environment into components that the patient's tissue can absorb, metabolize, respire, and/or excrete. Polymer chains are cleaved by hydrolysis and are eliminated from the body through the Krebs cycle, primarily as carbon dioxide and in urine. "Erodible" and "degradable" are intended to be used interchangeably herein.

The term "endoprosthesis" refers to any prosthetic device placed within the body. The term "endolumenal prosthesis" refers to any prosthetic device placed within a lumen or duct of the body. "Lumen" refers to any cavity or passageway within the body. For an endoprosthesis placed within a body lumen or duct in order to therapeutically treat the body lumen or duct, the therapeutic objective may include but is not limited to the objective of restoring or enhancing flow of fluids through a body lumen or duct. The objective may alternatively be the prevention of flow of fluid or other material through the body lumen or duct. An endolumenal prosthesis employing features of the invention may be of any structure or geometry, including but not limited to braided, tubular, slotted tube, fenestrated tube, or comprising one or more ring-like structures which may be joined to define a generally tubular device. An endolumenal prosthesis may be, for example, cut from a tube by excimer laser or other technique, or extruded, formed from a flat mold and rolled to form a tube, or injection molded according to techniques known in the art. An endolumenal prosthesis according to the invention may be fabricated from one or more shape memory polymers, comprised of segments selected for molecular weight, chemical composition and other properties, manufactured to achieve any desired geometries and processed to achieve sterilization, desired geometries and in vivo lifetime.

"Elasticity" refers to the ability of a material to repeatedly undergo significant tensile stress and strain, and/or compression stress and strain, and return to its original configuration.

"Shape memory" refers to the ability of a material to undergo structural phase transformation such that the material may define a first configuration under particular physical and/or chemical conditions, and to revert to an alternate configuration upon a change in those conditions. A polymer is a shape memory polymer if the original shape of the polymer is recovered by heating it above a shape recovering temperature (defined as the transition temperature of a soft segment) even if the original molded shape of the polymer is destroyed mechanically at a lower temperature than the shape recovering temperature, or if the memorized shape is recoverable by application of another stimulus. Such other stimulus may include but is not limited to pH, light, ultrasound, magnetic field, salinity, hydration, and others.

"Transition temperature" refers to the temperature above which a shape memory polymer reverts to its original memorized configuration.

The term "strain fixity rate" $R_f$ is a quantification of the fixability of a shape memory polymer's temporary form, and is determined using both strain and thermal programs. The strain fixity rate is determined by gathering data from heating a sample above its melting point, expanding the sample to 200% of its temporary size, cooling it in the expanded state, and drawing back the extension to 0%, and employing the mathematical formula:

$$R_f(N) = \epsilon_u(N)/\epsilon_m$$

where $\epsilon_u(N)$ is the extension in the tension-free state while drawing back the extension, and $\epsilon_m$ is 200%.

The "strain recovery rate" $R_r$ describes the extent to which the permanent shape is recovered:

$$R_r(N) = \frac{\varepsilon_m - \varepsilon_p(N)}{\varepsilon_m - \varepsilon_p(N-1)}$$

where $\epsilon_p$ is the extension at the tension free state.

As used herein, the term "segment" refers to a block or sequence of polymer forming part of the shape memory polymer. The terms hard segment and soft segment are relative terms, relating to the transition temperature of the segments. Generally speaking, hard segments have a higher glass transition temperature than soft segments, but there are exceptions.

A "switching segment" comprises a transition temperature and is responsible for the shape memory polymer's ability to fix a temporary shape.

A "thermoplastic elastomer" is a shape memory polymer comprising crosslinks that are predominantly physical crosslinks.

A "thermoset" is a shape memory polymer comprising a large number of crosslinks that are covalent bonds.

A "self-expanding" endoprosthesis has the ability to revert readily from a reduced profile configuration to a larger profile configuration in the absence of a restraint upon the device that maintains the device in the reduced profile configuration.

"Expandable" refers to a device that comprises a reduced profile configuration and an expanded profile configuration, and undergoes permanent plastic deformation upon the application of a mechanical force in order to transition from the reduced configuration to the expanded configuration.

"Expansion ratio" refers to the percentage increase in diameter of an endoprosthesis following conversion of the endoprosthesis from its reduced profile configuration to its expanded profile configuration. According to the invention, expansion ratios in excess of 500% are possible, and most often expansion ratios fall in the range of between 20% and 300%.

"Foreshortening ratio" refers to the percentage decrease in length of an endoprosthesis following conversion of the endoprosthesis from its reduced profile configuration to its expanded profile configuration.

The term "balloon assisted" refers to a self-expanding device the final deployment of which is facilitated by an expanded balloon.

The term "fiber" refers to any generally elongate member fabricated from any suitable material, whether polymeric, metal or metal alloy, natural or synthetic.

As used herein, a device is "implanted" if it is placed within the body to remain for any length of time following the conclusion of the procedure to place the device within the body.

The term "diffusion coefficient" refers to the rate by which a substance elutes, or is released either passively or actively from a substrate.

As used herein, the term "braid" refers to any braid or mesh or similar woven structure produced from between 1 and several hundred longitudinal and/or transverse elongate elements woven, braided, knitted, helically wound, or intertwined by any manner, at angles between 0 and 180° and usually between 45° and 105°, depending upon the overall geometry and dimensions desired.

Unless specified, suitable means of attachment may include by thermal melt, chemical bond, adhesive, sintering, welding, or any means known in the art.

Numerous polymers and polymer segments are suitable in practicing the invention herein Suitable synthetic polymer blocks include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof.

Examples of suitable polyacrylates include poly(methyl meth late), poly(ethyl methacrylate), poly(butyl methacrylate), poly(isobutyl methacrylate), poly(hexyl methacrylate), poly(isodecyl methacrylate), poly(lauryl methacrylate), poly (phenyl methacrylate), poly(methyl acrylate), poly(isopropyl acrylate), poly(isobutyl acrylate) and poly(octadecyl acrylate).

Examples of synthetic degradable polymer segments or polymers include polyhydroxy acids, polylactides, polyglycolides and copolymers thereof, poly(hydroxybutyric acid), poly(hydroxyvaleric acid), poly[lactide-co-epsilon-caprolactone)], poly[glycolide-co-(epsilon-caprolactone)], poly-(epsilon caprolactone) poly(pseudo amino acids), poly (amino acids), poly(hydroxyalkanoate)s, polyanhydrides, polyortho esters, and blends and copolymers thereof.

Rapidly erodible polymers such as poly(lactide-co-glycolide)s, polyanhydrides, and polyorthoesters, which have carboxylic groups exposed on the external surface as the smooth surface of the polymer erodes, also can be used. In addition, polymers containing labile bonds, such as polyanhydrides and polyesters, are well known for their hydrolytic reactivity. Their hydrolytic degradation rates can generally be altered by simple changes in the polymer backbone and their sequence structure.

According to an alternative aspect of the invention, degradable elastomers, or "biorubbers", such as, for example, poly (glycerol sebacate), synthesized according to any suitable methods, may be used.

Curable materials employed in the fabrication of some of the embodiments herein include any material capable of being able to transform from a fluent or soft material to a harder material, by cross-linking, polymerization, or other suitable process. Materials may be cured over time, thermally, chemically, or by exposure to radiation. For those materials that are cured by exposure to radiation, many types of radiation may be used, depending upon the material. Wavelengths in the spectral range of about 100-1300 nm may be used. The material should absorb light within a wavelength range that is not readily absorbed by tissue, blood elements, physiological fluids, or water. Ultraviolet radiation having a wavelength ranging from about 100-400 nm may be used, as well as visible, infrared and thermal radiation. The following materials are examples of curable materials: urethanes, polyurethane oligomer mixtures, acrylate monomers, aliphatic urethane acrylate oligomers, acrylamides, UV polyanhydrides, UV curable epoxies, and other UV curable monomers. Alternatively, the curable material can be a material capable of being chemically cured, such as silicone based compounds which undergo room temperature vulcanization.

According to the invention, numerous advantages are conferred upon endoprostheses in order to meet the clinical needs presented while treating strictures of the human body percutaneously. Firstly, a self-expanding device is disclosed, as is desirable for providing continual, consistent exertion of outward radial support following deployment, and which may eliminate the additional steps and accessories that may be required to deploy a balloon-expandable device. In addition, it may be possible to achieve a smaller crossing profile with a self-expanding device.

The use of polymeric materials in the fabrication of a self-expandable endolumenal prosthesis confers the advantages of improved flexibility, lumen compliance and conformability, permitting improved treatment in body lumens that may not be accessible to an endoprosthesis fabricated with a metal alloy. Further advantages of utilizing such a polymer to fabricate a self-expanding device include the ability to control the final diameter of the device more precisely, thereby avoiding potential injury to the lumen as a result of over-expansion. Shape memory polymeric devices may be designed to improve surface coverage of a lesion, thus providing greater support to the vessel, improving drug delivery across a given area and distributing applied stresses over a larger area than traditional metallic devices, and are therefore more compatible with soft tissue and the irregular morphology of a diseased lumen. And finally, expansion of a self-expanding polymeric device is less abrupt and less traumatic than that of a metal alloy device, again potentially decreasing the risk of injury to a lumen wall.

An endolumenal prosthesis comprising polymeric materials has the additional advantage of compatibility with magnetic resonance imaging, potentially a long term clinical benefit. Further, if the more conventional diagnostic tools employing fluoroscopic visualization continue as the technique of choice for delivery and monitoring, radiopacity can be readily conferred upon polymeric materials.

Shape memory polymers are highly versatile, and many of the advantageous properties listed above are readily controlled and modified through a variety of techniques. Several macroscopic properties such as transition temperature and mechanical properties can be varied in a wide range by only small changes in their chemical structure and composition.

Shape memory polymers are characterized by two features, triggering segments having a thermal transition $T_{trans}$ within the temperature range of interest, and crosslinks determining the permanent shape. Depending on the kind of crosslinks (physical versus covalent bonds), shape memory polymers can be thermoplastic elastomers or thermosets. By manipulating the types of crosslinks, the transition temperature, and other characteristics, shape memory polymers can be tailored for specific clinical applications.

More specifically, according the invention herein, one can the control shape memory behavior and mechanical properties of a shape memory polymer through selection of segments chosen for their transition temperature, and mechanical properties can be influenced by the content of respective segments. The extent of crosslinking can be controlled depending on the type of material desired through selection of materials where greater crosslinking, especially physical crosslinking, makes for a tougher material. In addition, the molecular weight of a macromonomeric crosslinker is one parameter on the molecular level to adjust crystallinity and mechanical properties of the polymer networks. An additional monomer may be introduced to represent a second parameter.

Further, the annealing process (comprising heating of the materials according chosen parameters including time and temperature) increases polymer chain crystallization, thereby increasing the strength of the material. Consequently, according to the invention, the desired material properties can be achieved by using the appropriate ratio of materials and by annealing the materials.

Highly elastic polymers have the additional advantages of the ability to undergo extensive temporary deformation while retaining the ability to readily revert to a permanent configuration. Devices fabricated from such polymers thereby have, for example, the ability to be delivered via very small diameter conduits as generally elongated and/or linear structures, yet able to form, for example, generally tubular and/or toroidal structures once released from the delivery conduit.

Additionally, the properties of polymers can be enhanced and differentiated by controlling the degree to which the material crystallizes through strain-induced crystallization. Means for imparting strain-induced crystallization are enhanced during deployment of an endoprosthesis according to the invention. Upon expansion of an endoprosthesis according to the invention, focal regions of plastic deformation undergo strain-induced crystallization, further enhancing the desired mechanical properties of the device, such as further increasing radial strength. The strength is optimized when the endoprosthesis is induced to bend preferentially at desired points.

The rate of degradation of a polymer can also be controlled. Non-linear erosion may result in a sudden release of potentially acidic degradation products from bulk material that may cause a strong inflammatory response. Further, high crystallinity of oligomer particles slows the erosion at the end of the process and may lead to the formation of fibrous capsules in vivo. In contrast, multiblockcopolymers show linear mass loss, resulting in a continuous release of degradation products. Consequently, a polymer may be prepared to exhibit linear erosion in order to decrease risk of restenosis. Further, polymers can be selected for which surface erosion is the primary mechanism of erosion, thereby preserving geometry and retention of mechanical strength.

The degree of crystallinity of the polymer or polymeric block(s) is between 3 and 800%, more often between 3 and 65%. The tensile modulus of the polymers below the transition temperature is typically between 50 MPa and 2 GPa (gigapascals), whereas the tensile modulus of the polymers above the transition temperature is typically between 1 and 500 MPa. The polymers described herein produce stresses in the range between 0.01 and 10 MPa during the transition to desired configuration, depending on the hard segment content. Such stresses are compatible with the mechanical stresses in soft tissue.

Though not limited thereto, some embodiments according to the invention comprise one or more therapeutic substances that will elute from the surface or the structure or prosthesis independently or as the prosthesis erodes. The cross section of an endoprosthesis member may be modified according to the invention in order to maximize the surface area available for delivery of a therapeutic from the vascular surface of the device. A trapezoidal geometry will yield a 20% increase in surface area over a rectangular geometry of the same cross-sectional area. In addition, the diffusion coefficient and/or direction of diffusion of various regions of an endoprosthesis, surface, may be varied according to the desired diffusion coefficient of a particular surface. Permeability of the luminal surface, for example, may be minimized, and diffusion from the vascular surface maximized, for example, by altering the degree of crystallinity of the respective surfaces.

According to the invention, such surface treatment and/or incorporation of therapeutic substances may be performed utilizing one or more of numerous processes that utilize carbon dioxide fluid, e.g., carbon dioxide in a liquid or supercritical state. A supercritical fluid is a substance above its critical temperature and critical pressure (or "critical point.")

In general, carbon dioxide may be used to effectively lower the glass transition temperature of a polymeric material to facilitate the infusion of pharmacological agent(s) into the polymeric material. Such agents include but are not limited to hydrophobic agents, hydrophilic agents and agents in particulate form. For example, following fabrication, an endoprosthesis and a hydrophobic pharmacological agent may be immersed in supercritical carbon dioxide. The supercritical carbon dioxide "plasticizes" the polymeric material, that is, it allows the polymeric material to soften at a lower temperature, and facilitates the infusion of the pharmacological agent into the polymeric endoprosthesis or polymeric coating of a stent at a temperature that is less likely to alter and/or damage the pharmacological agent.

Objectives of therapeutic substances incorporated into materials forming or coating an endoprosthesis according to the invention include reducing the adhesion and aggregation of platelets at the site of arterial injury, block the expression of growth factors and their receptors; develop competitive antagonists of growth factors, interfere with the receptor signaling in the responsive cell, promote an inhibitor of smooth muscle proliferation. Anitplatelets, anticoagulants, antineoplastics, antifibrins, enzymes and enzyme inhibitors, antimitotics, antimetabolites, anti-inflammatories, antithrombins, antiproliferatives, antibiotics, and others may be suitable.

According to the invention, endolumenal prostheses exhibiting desired characteristics may be fabricated in a number of ways. For example, endolumenal prostheses may be fabricated from copolymers synthesized to selectively exhibit a range of mechanical and thermomechanical properties. Lendlein, et al. report that such properties are readily modified by small molecular changes in the monomer selected and in the ratio of monomer to comonomer. (PNAS, Jan. 30, 2001, pp. 842-847, vol. 98 No. 3.) A copolymer synthesized from two oligo(ε-caprolactone) dimethacrylates having different molecular weights of 2,000 (PCLDMA2000) and 10,000 (PCLDMA10,000) and n-butyl acrylate is discussed. PCLDMA2000 and PCLDMA10,000 were each coupled with n-butyl acrylate in different ratios. The results show variation of thermal properties and mechanical properties depending upon the percentage of n-butyl acrylate incorporated and the molecular weight of PCLDMA. The percentage of comonomer ranged from 0-90%, and for formulating copolymers for use in fabricating endolumenal prostheses, most often will be in the range of 20-70%.

As an example of the variations, the percentage elongation of the copolymer under stress is influenced by the incorporation of n-butyl acrylate for both, increasing the percentage up to a certain ratio of n-butyl acrylate, and is significantly greater in the higher molecular weight copolymer. (553% versus 28%.) The elastic modulus (Young's modulus) of a copolymer synthesized decreased with the higher ratio of n-butyl acrylate and was significantly higher in the higher molecular weight copolymer (1.6 MPa versus 49 MPa at 38% and 39% n-butyl acrylate respectively).

Lendlein et al. also quantified the shape memory effect for polymer networks containing PCLDMA10000. Heating a sample above the melting point to 70° C., expanding the polymer to 200% ($\epsilon_m$), cooling it to 0° C. and drawing back the extension to 0%, and again warming the sample up, the strain fixity rate $R_f$ (the fixability of the temporary form) and the strain recovery rate $R_r$ (the extent the permanent shape is recovered) can be determined. The material showed excellent shape memory behaviors, with the average strain recovery rates between 93% and 98%, increasing with the content of n-butyl acrylate. The average strain fixity rate was about 95% but began to decrease when percentage of n-butyl acrylate surpassed 50%.

Following from the foregoing discussion, the behavior of a shape memory polymer can be predicted and controlled according to, among other factors, the selected ratio of monomer to comonomer. According to the invention, by selecting the appropriate values for the parameters disclosed, a copolymer is synthesized to exhibit the shape memory behavior desired for use in fabrication of a device for a particular clinical application, such as, for example, in the fabrication of an endolumenal prosthesis as described above.

Lendlein et al. also report that macrodiols with different thermal characteristics may be synthesized via ring opening polymerization of cyclic diesters or lactones with low molecular weight diol as initiator and purified. (www.sciencexpress.org(25Apr. 2002/Page1/10.1126science. 1066102). Oligo(ε-caprolactone) diol was chosen as a precursor for the switching segments having a melting transition temperature. Crystallizable oligo(p-dioxanone) diol was chosen as hard segment. Melting temperature of a polymer may be slightly affected by the content of hard and soft segments. The melting point and glass transition temperature of the hard segment are generally at least 10° C., and often 20° C., higher than the transition temperature of the soft segment. The transition temperature of the hard segment is between −60° C. and 270° C., and more often between 30° C. and 150° C. The ratio by weight of the hard segment to soft segments is between about 0:100 and 83:17, and most often between 20:80 and 80:20. The two macrodiols are coupled in a second step in the range of proportions as noted above. Shape memory behavior and the ranges in thermomechanical properties of the resulting copolymers are consistent with those discussed above. Consequently, depending upon the desired properties of a material and device manufactured therefrom, a particular ratio of monomer and comonomer can be selected accordingly.

Alternatively, endoprostheses exhibiting the desired mechanical properties may be fabricated from an elastic block copolymer. Wang et al. report the synthesis of poly (glycerol-sebacate), a tough bioerodible elastomer with excellent biocompatibility. (Nature Biotechology, Volume 20, June 2002, http://biotech.nature.com), forming a crosslinked, three-dimensional network of random coils, analogous to vulcanized rubber. Combining such a polymer with an aromatic block capable of reversible shape memory behavior results in a copolymer exhibiting both high elasticity and thermally initiated shape memory properties. The harder segment of the copolymer will form a crystalline segment that can be overcome by thermal energy, thereby conferring reversible shape memory behavior upon the material. The elastomeric portion confers on the material (and consequently the endoprosthesis) the ability to undergo significant temporary mechanical stress and temporary deformation during, for example, the delivery process. A polycondensation reaction between an aromatic block selected for its particular molecular weight, and transition temperature, sebacic acid, and glycerol, for example, all at desired molar ratios to achieve the behavior desired for a particular clinical setting, may be performed, and an endolumenal prosthesis fabricated from the copolymer.

As another alternative, endolumenal prostheses that readily and extensively convert between two configurations may be fabricated from a high modulus elastomer. A high-modulus elastomer may be synthesized by polycondensation of polymers selected for their high degree of elasticity. Such copolymers may surpass the modulus of poly(glycerol-sebacate), allowing even greater elastic deformation during, for example, the delivery process, while permitting an endolumenal prosthesis to revert to its permanent, unconstrained configuration. According to the invention, an elastomer exhibiting a modulus as much as 100 times the modulus of poly(glycerol-sebacate) may be achieved. An endoprosthesis fabricated from the foregoing material may alternatively be coated with a hydrogel which, upon exposure to an aqueous solution, swells, and/or loses its stiffness, thereby removing constraints from the endolumenal prosthesis which will readily revert to its permanent configuration.

An additional alternative embodiment comprises a hydrogel that undergoes extensive increase in size upon exposure to an aqueous medium to convert from a reduced, delivery configuration to a deployed configuration.

EXAMPLE 1

1) Synthesis: Elastic block copolymers were synthesized by polycondensation reaction between terephthalic acid, sebacic acid, and glycerol. The molar ratio of the two acids is 40:60 terephthalic:sebacic. Dimethyl terephthalate was synthesized by refluxing terephthalic acid in methanol in the presence of 5 mole % concentrated $H_2SO_4$ overnight. After solvent removal under vacuum, the crude product was purified by extraction and vacuum distillation, and stored anhydrously. Dry dimethyl terephthalate and anhydrous glycerol were heated at 150° C. in an inert atmosphere for 8 hours before sebacic acid was added. Catalytic amount of zinc acetate was added to the mixture, and it was heated for another 24 hours. The viscous liquid obtained was poured into a Teflon mold while still hot, transferred into a vacuum oven, and cured at 180° C., 50 mTorr for 12 h. The polymer [poly (glycerol sebacate-co-terephthalate)] film was cut into square prism of about 7×7×3 mm. Three specimens were mounted a mechanical tester and subjected to unconstrained compression. The polymer is highly elastic, as demonstrated by the low plastic deformation when compressed repeatedly. In addition, the polymer maintained its integrity even when compressed to 80% (See FIG. 3).

2) Preliminary shape memory behavior: A thin polymer stripe was used for the test The permanent shape is a straight rod. The polymer was locked into a spiral shape when wrapped around a mandrel and held in a spiral configuration at 120° C. for 5 mm. Upon release of the external force, the spiral shape was maintained. When heated again to 120° C., the spiral unwound partially. Theoretically, the aromatic block of the copolymer should be able to give the polymer a fully reversible shape memory behavior. With further modification, such as increasing the aromatic block length, (through increased reaction time, and/or the addition of a catalyst) we may obtain a completely reversible shape memory polymer. Such a material can be fashioned into a stent, which can be delivered as a rod, and will wind into a spiral upon exposure to body temperature.

EXAMPLE 2

A high-modulus elastomer was synthesized by polycondensation of equimolar amount of dimethyl terephthalate (see example 1) and glycerol. Anhydrous dimethyl terephthalate (5 g) and 2.37 g of anhydrous glycerol were heated at 150° C. in an inert atmosphere for 8 hours before catalytic amount of zinc acetate was added to the mixture. The reaction mixture was heated for another 12 hours. Alternatively, the polymer can be synthesized by polycondensation of terephthaloyl chloride or terephthalic acid with glycerol. The resulted polymer was poured into a Teflon mold, and transferred into a vacuum oven. The polymer was cured for 24 hours at 180 degrees C. and 50 mTorr. The cured polymer was cut into 5×5×3 mm blocks, and mounted on a mechanical analyzer. An unconstrained compression test was used to characterize the mechanical propertires of the polymer. The modulus is 115 Mpa, about 100 times higher than that of poly(glycerol sebacate), yet still elastic enough to withstand more than 30% compression (See FIG. 4). It is feasible to fabricate fibers from this polymer, which can be used to make endoprostheses, or to mold endoprostheses from the material that can be delivered through a narrow conduit in an elastically deformed, or collapsed state. Because the elastomer has a relatively high modulus, once the restraints from the conduit are removed, the endoprostheses would readily convert back into an expanded state.

EXAMPLE 3

High molecular weight hyaluronic acid (HA, 1 g) was dissolved in D1 water (10 ml), 20 ml of 10% aqueous NHS ester activated PEG-methacrylate (MW 400) was added under constant stirring at room temperature. The solution was stirred for 6 hours. Byproducts and unreacted staring materials were removed by dialysis (MWCO: 1000). Water was removed from the purified product by lyophilization. Pegylated HA (500 mg) was dissolved in 10 ml distilled water, then 60 µl of 2% 2,2-dimethoxy-2-phenylacetophenone (initiator) in 1-vinyl-2-pyrrolidinone was added under stirring at room temperature. The mixture was exposed to 365 nm UV light for 20 min, and then water was removed by lyophilization. When the resulted polymer was exposed to an aqueous solution, it can swell up to 50 times, as determined by weight change. An endoprosthesis made of this material can be delivered to the treatment site, and expand in situ.

EXAMPLE 4

A thin layer of concentrated, freshly prepared 1-ethyl-3-(3-methylaminopropyl) carbodiimide hydrocloride (EDC) solution was applied on top of a 100 µm thick poly(glycerol-sebacate) (PGS) strip. A 200 µm thick dry crosslinked hyaluronic acid (see example 3) strip was put immediately on top of the surface. The layers were kept undisturbed for 3 hours. When the laminated structure was put in water, the crosslinked hyaluronic acid layer started to swell, and the structure curled up within 30 min. It is feasible to make a stent with this material with the HA hydrogel on the outside. Once delivered to the treatment site, the stent is exposed to an aqueous media such as body fluid, it will change shape and curl up. It is possible to take advantage of such geometrical change to fashion a stent that can expand to the desired shape in situ.

While particular forms of the invention have been illustrated and described above, the foregoing descriptions are intended as examples, and to one skilled in the art will it will be apparent that various modifications can be made without departing from the spirit and scope of the invention.

We claim:

1. A method of manufacturing a shape memory polymer endolumenal prosthesis comprising the steps of:
    synthesizing poly(glycerol sebacate-co-terephthalate) via a polycondensation reaction method, said reaction method comprising the steps of preparing a reaction mixture, introducing a catalyst, and heating for at least twelve hours following the introduction of a catalyst;
    curing said poly(glycerol sebacate-co-terephthalate); and
    forming a generally tubular endolumenal prosthesis from said poly(glycerol sebacate-co-terephthalate).

2. The method according to claim 1 wherein said step of curing the poly(glycerol sebacate-co-terephthalate) comprises placing said poly(glycerol sebacate-co-terephthalate) into a mold and placing said mold into an oven at 180° C. at 50 mTorr for at least twelve hours.

3. The method according to claim 1 wherein said step of preparing a reaction mixture comprises:
    combining dimethyl terephthalate and anhydrous glycerol;
    heating the combination at 150° C. for 8 hours or more; and
    adding sebacic acid.

4. The method according to claim 1 wherein said catalyst is zinc acetate.

5. The method according to claim 1 wherein said mixture is heated for 24 hours following the introduction of a catalyst.

6. The method according to claim 1 further comprising the steps of:
    setting a permanent shape for said endoprosthesis;
    setting a temporary shape for said endoprosthesis.

7. The method according to claim 6 wherein the method further comprises the step of laminating said endoprosthesis with a hydrogel after setting the temporary shape.

* * * * *